United States Patent
Bretmersky

(10) Patent No.: US 7,231,805 B2
(45) Date of Patent: Jun. 19, 2007

(54) BUBBLE DETECTION WITH TEMPERATURE COMPENSATION

(75) Inventor: Carl A. Bretmersky, North Olmsted, OH (US)

(73) Assignee: Nordson Corporation, Westlake, OH (US)

( * ) Notice: Subject to any disclaimer, the term of this patent is extended or adjusted under 35 U.S.C. 154(b) by 228 days.

(21) Appl. No.: 10/980,490

(22) Filed: Nov. 3, 2004

(65) Prior Publication Data

US 2006/0090538 A1    May 4, 2006

(51) Int. Cl.
    *G01N 7/00*    (2006.01)
(52) U.S. Cl. .................................... 73/19.01
(58) Field of Classification Search ............... 73/19.01, 73/19.05
    See application file for complete search history.

(56) References Cited

U.S. PATENT DOCUMENTS

| | | | | |
|---|---|---|---|---|
| 4,651,556 A | * | 3/1987 | Seaman | 73/19.03 |
| 4,779,762 A | * | 10/1988 | Klein et al. | 222/52 |
| 5,054,650 A | * | 10/1991 | Price | 222/1 |
| 5,056,034 A | * | 10/1991 | Rucki et al. | 702/46 |
| 5,182,938 A | | 2/1993 | Merkel | |
| 5,488,854 A | * | 2/1996 | Kawanabe et al. | 73/19.05 |
| 5,551,305 A | * | 9/1996 | Farchi et al. | 73/861.04 |
| 6,060,320 A | * | 5/2000 | Dorenkott et al. | 436/54 |
| 6,094,966 A | * | 8/2000 | Papen et al. | 73/1.74 |
| 2004/0065143 A1 | * | 4/2004 | Husher | 73/64.53 |

* cited by examiner

*Primary Examiner*—Hezron Williams
*Assistant Examiner*—John Fitzgerald
(74) *Attorney, Agent, or Firm*—Calfee, Halter & Griswold, LLP

(57) ABSTRACT

Bubble detection apparatus and method for a liquid dispensing system includes temperature compensation for increasing accuracy of the bubble detection as temperature of the liquid varies. In one embodiment, temperature changes cause corresponding changes in the liquid viscosity. A reference value or pressure signal that is used in a comparator circuit is adjusted or compensated for temperature changes of the liquid. The comparator compares pressure signals to the reference to detect bubbles in the liquid being dispensed.

23 Claims, 3 Drawing Sheets

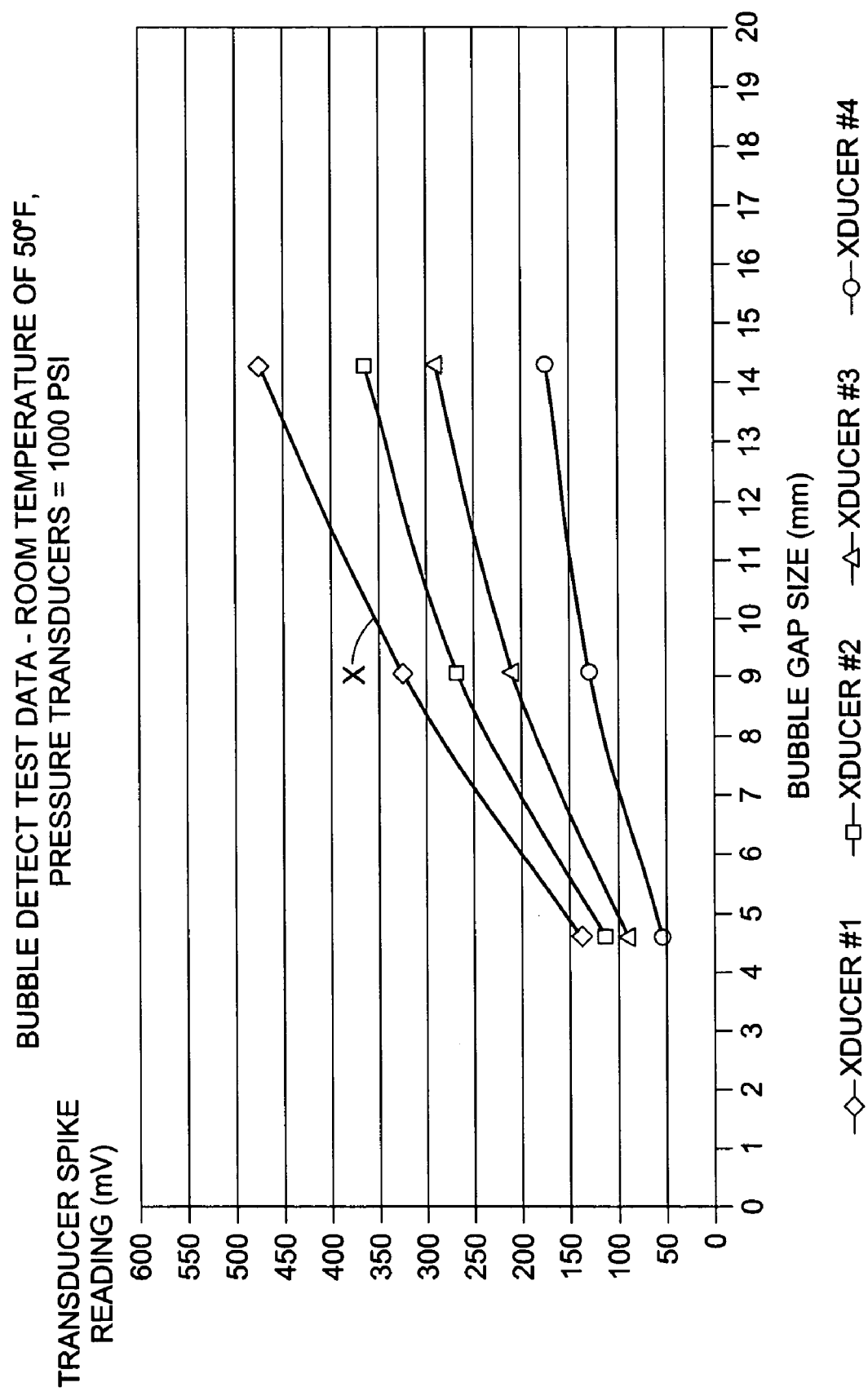

BUBBLE DETECTION WITH TEMPERATURE COMPENSATION

The invention relates generally to detecting bubbles in liquid material dispensing apparatus. More particularly the invention relates to compensating for viscosity changes in the dispensed liquid.

BACKGROUND OF THE INVENTION

Liquid dispensing systems are used for applying liquid materials to a substrate or surface. In many applications, the presence of an air bubble can compromise the quality of the liquid bead that is applied. Accordingly, various techniques have been employed to detect bubbles in the liquid material. U.S. Pat. No. 5,182,938 (the "'938" patent hereinafter) describes method and apparatus for detecting bubbles in a liquid dispensing system, the entire disclosure of which is fully incorporated herein by reference.

SUMMARY OF THE INVENTION

The invention contemplates viscosity related compensation for bubble detection processes used in a liquid dispensing system. In accordance with one aspect of the invention, viscosity changes of the liquid are directly or indirectly determined. In one embodiment, a predeterminable relationship between viscosity and temperature is used. Viscosity changes can decrease the accuracy of a pressure based bubble detection apparatus because pressure variations can occur due to temperature and not necessarily due to presence of a bubble. In one embodiment of the invention, a liquid pressure signal is produced and compared with a reference signal. The reference signal or the pressure signal is changed in relation to temperature. By compensating for viscosity changes, accuracy of the pressure based technique is maintained.

In accordance with another aspect of the invention, temperature and/or viscosity compensation is used with a pressure based bubble detection system. In one embodiment, a pressure based signal is compared to a reference level. A look-up table or other stored characterization of the liquid is used to adjust the reference signal based on temperature. The adjustment of the reference as a function of temperature may be empirically determined. Various factors can be used to determine the adjustment needed, including the location in the flow path where the pressure is being detected and where in the apparatus temperature is being determined. Temperature in the ambient environment may optionally be used.

The invention contemplates the methods embodied in the use of such apparatus, and furthermore contemplates a method for detecting bubbles in a liquid dispensing system using viscosity compensation such as for example by temperature. In one embodiment a method for detecting bubbles in a liquid dispensing system comprises the steps of detecting pressure variations in the liquid and producing a pressure signal related thereto, comparing the pressure signal to a reference and producing a bubble detection signal, and adjusting the reference in relation to changes in temperature.

These and other aspects and advantages of the present invention will be understood from the following description of the exemplary embodiments in view of the accompanying drawings.

BRIEF DESCRIPTION OF THE DRAWINGS

FIGS. 2 and 3 illustrate variations of measured pressure versus bubble size at two temperatures;

DETAILED DESCRIPTION OF EXEMPLARY EMBODIMENTS

Figure 1:
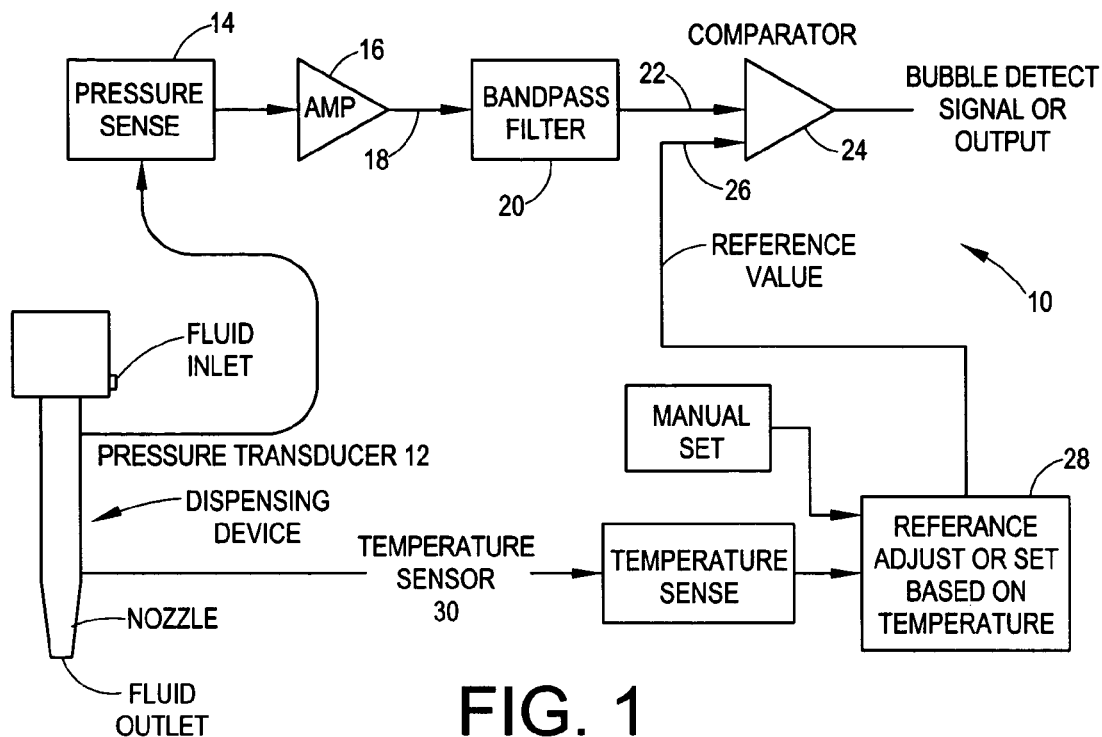
FIG. 1 is a functional block diagram of an exemplary embodiment of the invention.

In accordance with the invention, accuracy of bubble detection can be improved by including compensation for viscosity as part of the detection apparatus and method. Temperature changes, for example, cause corresponding or predictable viscosity changes in the liquid. These viscosity changes affect measurements of the bubble in the liquid and therefore can cause false readings of bubbles, or missed bubbles.

While the invention is described herein with respect to specific embodiments, such descriptions are intended to be exemplary in nature and not to be construed in a limiting sense. The invention may be realized in many different forms, including various hardware, software and circuit variations while achieving the benefits and advantages of the invention. For example, the exemplary embodiment uses a determinable relationship between temperature and viscosity to adjust a reference. Thus, by measuring temperature of or related to the liquid, the reference can be adjusted so that pressure based bubble detection is more accurate. However, in an alternative embodiment the viscosity characteristic may be determined by other than a temperature measurement, for example by ultrasonic measurements. Still further, while the exemplary embodiments herein described a pressure-based bubble detection system, such description should not be construed in a limiting sense. Other detection techniques can utilize the advantage of the present invention. For example, ultrasonic energy is sometimes used for bubble detection. Ultrasonic sensors will be influenced by viscosity changes in the measured fluid. Thus the invention is more broadly applicable to bubble detection processes that are influenced by viscosity of the liquid.

While various aspects of the invention are described and illustrated herein as embodied in combination in the exemplary embodiments, these various aspects may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, software, hardware, control logic and so on may be described herein, such descriptions are not intended to be a complete or exhaustive list of available alternative embodiments, whether presently known or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, exemplary or representative values and ranges may be included to assist in understanding the present invention however, such values and ranges are not to be construed in a limiting sense and are intended to be critical values or ranges only if so expressly stated.

FIG. 1 illustrates an exemplary embodiment of the invention. In this example, a pressure-based bubble detection system 10 includes a pressure transducer 12 that is disposed in an appropriate location of a liquid dispensing device. For example, the transducer 12 can be disposed near a nozzle of the device. In some cases the transducer 12 can detect pressure at a location outside the dispensing device if its relationship to pressure inside the device is known or proportional. The transducer 12 can be any suitable device. One such transducer is model BPR321CR available from Sensotec. The transducer produces an electrical output signal 14 such as a voltage signal that is related to the pressure of the liquid. This pressure signal is input to an amplifier circuit 16 to boost the signal strength. The amplifier 16 may also be used to filter out pressure signals of insufficient amplitude, such as false signals. The amplifier 16 may be conventional in design such as an inverting differential gain operational amplifier, as is well known to those skilled in the art. The amplifier output 18 is input to a bandpass filter circuit 20. The bandpass filter can be conventional in design as is well known to those skilled in the art and is used to filter transient pressure signals. Additional detail as to the bandpass filter and the amplifier can be obtained for example from the '938 patent and form no particular aspect of the present invention, other than as known signal processing techniques for analyzing the pressure transducer output.

Figure 3:
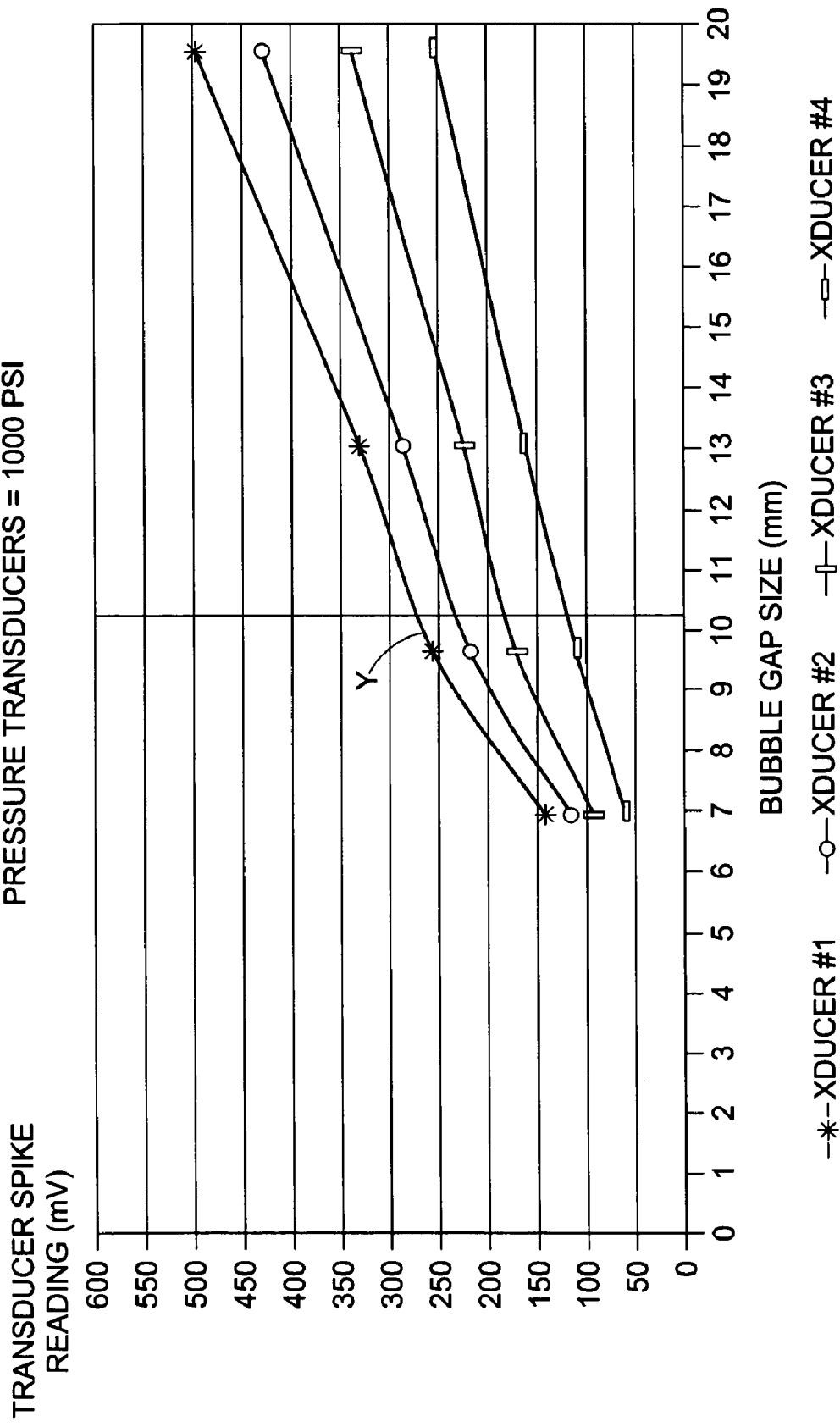

The output 22 of the bandpass filter is input to a comparator circuit 24 that compares the amplitude of the amplified and filtered transducer pressure signal to a reference 26. The reference is selected based on empirical knowledge of a signal amplitude that corresponds to a bubble in the liquid. A temperature compensation function 28 is provided that adjusts the reference 26 as a function of viscosity. For example, empirical data can be collected that characterizes the relationship between the pressure transducer signal and bubble size. This data can also be obtained at different temperatures. FIGS. 2 and 3 illustrate such representative data. By knowing the relationship between temperature and the changes in the detected pressure, as indicated by the pressure transducer output, the reference signal is adjusted so that the comparator more accurately compares the transducer output to a more accurate reference.

A comparison of FIGS. 2 and 3 illustrates that as temperature increases, the transducer output signal decreases for a given bubble size. For example, point X in FIG. 3 corresponds approximately to a 10 millimeter bubble with a liquid temperature of about 50 degrees Fahrenheit that produces an output signal from the transducer of about 350 millivolts. But from FIG. 3, the same size bubble produces an output from the transducer of about 260 millivolts (point Y). This can be understood as a change in viscosity in which increasing temperature decreases viscosity and hence reduces system pressure. The corresponding transducer output signal is still valid but of lesser amplitude, simply due to temperature and viscosity changes. Therefore, the transducer output can still be used to detect bubbles by adjusting the reference that is used to determine a 'valid' pressure signal indicative of a bubble.

Figure 5:
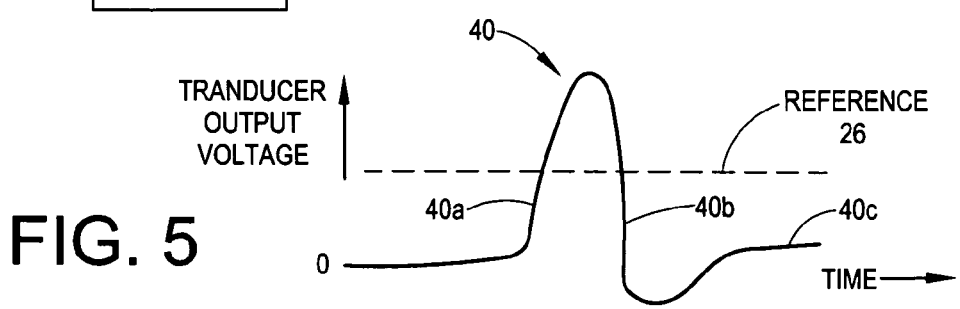
FIG. 5 is a graphical representation of a typical pressure pulse (exemplified as a pressure transducer output voltage signal) produced by a bubble or gap in the liquid flow.

FIG. 5 illustrates the basic comparison. A typical bubble or gap produces a transient in the pressure transducer signal 40 that typically has a significant rise 40a then a fall off 40b until pressure returns to ambient 40c. A reference level 26 can be used to determine that if the amplitude is greater than the reference then the signal corresponds to a bubble. Various additional filtering schemes can be used to further validate the transducer signals, such as for example disclosed in the '938 patent. As the signal strength changes from the pressure transducer due to viscosity changes, as a result of temperature variation for example, the reference level 26 can be adjusted or set higher or lower as needed to more accurately determine if the signal 40 corresponds to an actual bubble.

The temperature compensation function 28 may be realized in many different ways, including in hardware, circuitry, software and even manual adjustment. In the exemplary embodiment of FIG. 1, the temperature compensation function 28 is realized in the form of a temperature sensor 30 that may be, for example, disposed near the pressure sensor 12. A look-up table is used to store the relationship between the liquid temperature and the adjustment needed, or actual value thereof, of the reference 26.

Although temperature measurement is a straight forward and simple way to determine an adjustment to the reference signal, in some applications it may be desirable to perform additional or alternative measurements. Viscosity changes can be determined by techniques other than just temperature measurement, but the adjustment to the reference 26 would be corresponding to a temperature based system. For example, viscosity changes can be detected by ultrasonics, flow rate measurements, volume dispensed per unit time and so on.

The invention will find application in many different bubble detection apparatus, including the apparatus disclosed in the '938 patent. Again, as in the exemplary embodiment, a temperature sensor may be used to detect temperature of the liquid and the reference values adjusted as a function of the temperature.

Figure 4:
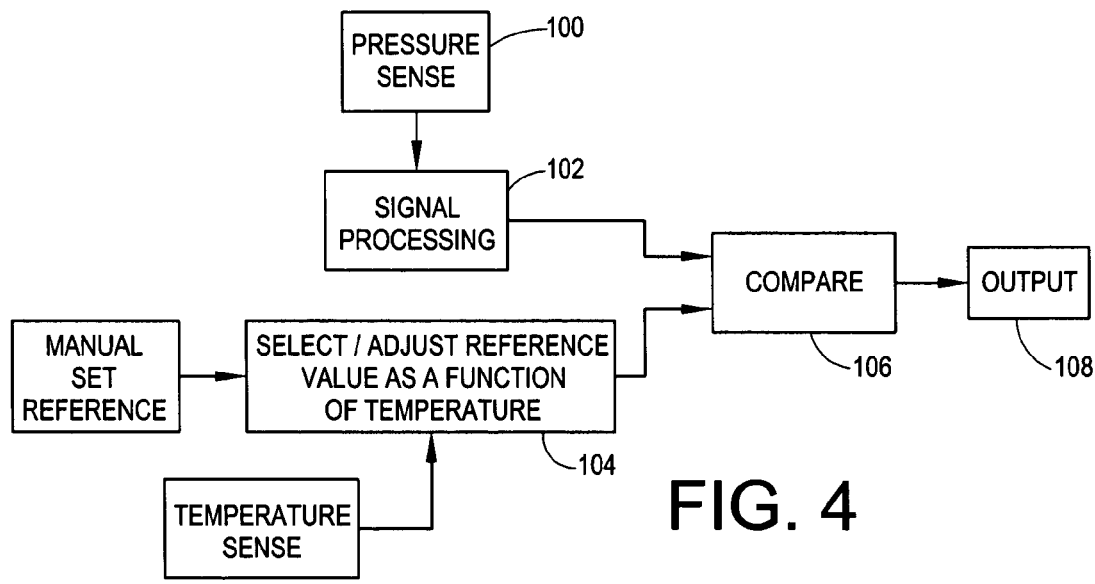
FIG. 4 is a simplified flow diagram for one embodiment of the invention.

FIG. 4 illustrates an exemplary flow chart of a process for temperature compensation with pressure-based bubble detection. At step 100 the pressure of the liquid is determined. At step 102 the pressure value is optionally processed to improve the quality of the value, such as for example signal processing of a transducer voltage output signal. At step 104 a reference value is selected as a function of detected temperature. At step 106 the pressure value is compared with the reference and at step 108 a bubble detection output is produced when the comparison at step 106 indicates the presence of a bubble. As an alternative, the reference value at step 104 can be adjusted by a suitable factor, rather than accessing the actual reference value. This for example could be realized with circuitry or even manually rather than the need for a look-up table. Still as a further alternative it may be possible for some liquids to use a mathematical equation to establish the adjustment to the reference value as a function of temperature of the liquid.

Note that FIGS. 2 and 3 show a family of curves. This illustrates the sensor readings for different physical locations of the sensor in the dispensing device or along the flow path of the liquid. Different locations can produce different output signal strengths from the transducer. The temperature compensation function of the present invention thus can be used with different locations of the pressure sensor and/or the temperature sensor. Typically the pressure transducer, like the temperature sensor, will be positioned near the nozzle to provide higher sensitivity to the bubble as it passes through and exits the nozzle but this location is not required for either sensor.

It is important to note that for both FIG. 1 and FIG. 4, the initial selection or setting of the reference value may be, and often is, a manual operation or input from the operator. For example, any convenient input device may be used for the operator to select the initial reference value, and then the temperature compensation function 28, 104 can be used to adjust the reference level as needed for temperature changes. Manual or operator selection of the initial value is often useful because different applications of the dispensing device may require different levels of sensitivity to bubble size. Manual setting can also be used to adjust for whether the system is starting from an overnight cold start, or warm weather start and so on.

It is important to note that the viscosity or temperature adjustment or compensation to the reference 26 may alternatively be replaced by a viscosity or temperature based adjustment or compensation of the pressure signal. In other words, the comparator output will be compensated for temperature or viscosity changes when either the reference value is adjusted or the sensor output signal is adjusted. The comparator circuit in this regard can be thought of as a compensator that takes the pressure signal and not only compares it to a reference to detect the presence of a bubble, but in effect compensates the pressure signal for changes in viscosity/temperature of the liquid material. This compensation can be understood and realized as a temperature/viscosity compensation of the pressure signal, the reference value or both.

The invention has been described with reference to the preferred embodiment. Modifications and alterations will occur to others upon a reading and understanding of this specification and drawings. The invention is intended to include all such modifications and alterations insofar as they come within the scope of the appended claims or the equivalents thereof.

I claim:

1. Apparatus for detecting bubbles in a liquid dispensing system, comprising:
   a first circuit that detects pressure variations in the liquid and produces a pressure signal related thereto,
   a second circuit that compares said pressure signal to a reference and produces a bubble detection signal,
   a temperature compensation circuit that adjusts said reference in relation to a detected temperature.

2. The apparatus of claim 1 wherein said first circuit comprises a pressure transducer that detects pressure of the liquid near a dispensing nozzle.

3. The apparatus of claim 1 wherein said second circuit comprises a comparator.

4. The apparatus of claim 1 wherein said temperature compensation circuit comprises a look-up table that provides a reference adjustment value as a function of temperature.

5. The apparatus of claim 1 wherein said temperature compensation circuit comprises a look-up table that relates liquid viscosity or temperature to said reference.

6. The apparatus of claim 1 wherein said temperature compensation circuit adjusts said reference based on a detected temperature of the liquid.

7. The apparatus of claim 1 comprising a bandpass filter that receives said pressure signal and filters out non-bubble related pressure transients.

8. The apparatus of claim 7 wherein said second circuit receives an output from said bandpass filter.

9. Apparatus for detecting bubbles in a liquid dispensing system, comprising:
   first means for detecting pressure variations in the liquid and producing a pressure signal related thereto,
   second means for comparing said pressure signal to a reference and producing a bubble detection signal,
   third means for adjusting said reference in relation to a detected temperature.

10. The apparatus of claim 9 wherein said second means comprises a comparator.

11. The apparatus of claim 9 wherein said third means comprises a look-up table that relates liquid temperature to said reference.

12. The apparatus of claim 9 wherein said third means comprises a look-up table that relates liquid viscosity to said reference.

13. Apparatus for detecting bubbles in a liquid dispensing system, comprising:
   a first circuit that detects pressure variations in the liquid and produces a pressure signal related thereto,
   a second circuit that compares said pressure signal to a reference and produces a bubble detection signal,
   said second circuit adjusting said reference in relation to viscosity changes of the liquid and a detected temperature.

14. The apparatus of claim 13 wherein said second circuit comprises at least one of the following: a) a look-up table that relates liquid temperature to the reference, and b) a look-up table that relates liquid viscosity to the reference.

15. The apparatus of claim 13 wherein said second circuit comprises a comparator circuit.

16. A method for detecting bubbles in a liquid dispensing system, comprising the steps of:
   detecting pressure variations in the liquid and producing a pressure signal related thereto,
   comparing said pressure signal to a reference and producing a bubble detection signal,
   adjusting said reference in relation to changes in a detected temperature.

17. The method of claim 16 wherein the adjusting step includes adjusting said reference in relation to a temperature dependent characteristic of the liquid.

18. The method of claim 17 wherein said temperature-dependent characteristic is viscosity.

19. The method of claim 17 wherein said temperature-dependent characteristic is actual temperature of the liquid.

20. The method of claim 17 comprising the step of storing a table that relates said characteristic to said reference.

21. A method for detecting bubbles in a liquid dispensing system, comprising the steps of:
   detecting variations in the liquid and producing a signal related thereto,
   comparing said signal to a reference and producing a bubble detection signal,
   adjusting said reference in relation to a detected temperature.

22. A method comprising the steps of:
   generating a signal in response to the presence or absence of a bubble in a liquid material within a liquid dispensing system;
   compensating the signal as a function of changes in the viscosity of the liquid material in relation to a detected temperature;
   comparing the compensated signal to a reference.

23. An apparatus for detecting bubbles in a liquid dispensing system, comprising:
- a detector for detecting pressure variations in a liquid and generating a pressure signal related thereto;
- a comparator for comparing the pressure signal to a reference and producing a bubble signal;
- a sensor for detecting temperature and generating a temperature signal; and
- a compensator for adjusting one or both of said reference and said pressure signal in response to said temperature signal.

* * * * *